(12) United States Patent
Parks et al.

(10) Patent No.: US 8,901,090 B2
(45) Date of Patent: Dec. 2, 2014

(54) METHOD OF TREATING OTITIS EXTERNA USING MACROCYCLIC LACTONE COMPOUND

(75) Inventors: L. Dean Parks, Ocala, FL (US); Jeffrey D. Parks, Ormond Beach, FL (US)

(73) Assignee: Galderma S.A., Cham (CH)

( * ) Notice: Subject to any disclaimer, the term of this patent is extended or adjusted under 35 U.S.C. 154(b) by 0 days.

(21) Appl. No.: 13/823,330

(22) PCT Filed: Oct. 14, 2011

(86) PCT No.: PCT/US2011/056330
§ 371 (c)(1),
(2), (4) Date: Mar. 14, 2013

(87) PCT Pub. No.: WO2012/054331
PCT Pub. Date: Apr. 26, 2012

(65) Prior Publication Data
US 2013/0178434 A1    Jul. 11, 2013

Related U.S. Application Data

(60) Provisional application No. 61/394,906, filed on Oct. 20, 2010.

(51) Int. Cl.
*A61K 31/70* (2006.01)
*A61K 31/7048* (2006.01)
*A61K 9/00* (2006.01)
*A61K 9/06* (2006.01)
*A61K 31/365* (2006.01)
*A61K 47/10* (2006.01)
*A61K 47/14* (2006.01)
*A61K 47/26* (2006.01)

(52) U.S. Cl.
CPC ........... *A61K 31/7048* (2013.01); *A61K 9/0046* (2013.01); *A61K 9/06* (2013.01); *A61K 31/365* (2013.01); *A61K 47/10* (2013.01); *A61K 47/14* (2013.01); *A61K 47/26* (2013.01)
USPC .......................................................... 514/30

(58) Field of Classification Search
CPC .................................................. A61K 31/7048
See application file for complete search history.

(56) References Cited

U.S. PATENT DOCUMENTS 4,159,719 A * 7/1979 Haerr ............................. 604/514
6,797,701 B2   9/2004 Lukas et al.

FOREIGN PATENT DOCUMENTS

CA          2551833 A1    8/2005
WO    WO 2010011609 A2    1/2010

OTHER PUBLICATIONS

Supplemental European Search Report of counterpart European Application No. 11834899.4, Mar. 1, 2012.
Page et al, "Observations on Topical Ivermectin in the Treatment of Otoacariosis, Cheyletiellosis, and Toxocariosis in Cats" Canadian Veterinary Journal, vol. 41, No. 10, Oct. 2000, pp. 773-776 The whole document.
Msolla et al, "Treatment of Bovine Parasitic Otitis Using Ivermectin" Trop. Anim. Hlth. Prod., vol. 17, No. 3, Jan. 1985, 166-168 The whole document.
Waly et al, "Efficacy of Ivermectin Injection, Canaural Ear Drops and Frontline Combo in Treatment of Earmite-Induced Otitis Externa in Cats" Journal of Veterinary International Medicine, vol. 27, No. 3, May 2013, p. 751 The whole document.
International Search Report and Written Opinion of International Search Authority of PCT/US2011/056330, Mar. 1, 2012.

* cited by examiner

*Primary Examiner* — Elli Peselev
(74) *Attorney, Agent, or Firm* — CUSPA Technology Law Associates, P.A.; Yi Li

(57) ABSTRACT

A method of treating otitis externa is disclosed. The method includes topically applying an otic composition containing an effective amount of one or more macrocyclic lactone compounds, including avermectin compounds or milbemycin compounds and a pharmaceutically acceptable carrier into the external auditory canal and the auricle of an affected ear of an individual suffering from otitis externa.

21 Claims, No Drawings

METHOD OF TREATING OTITIS EXTERNA USING MACROCYCLIC LACTONE COMPOUND

FIELD OF THE INVENTION

The present invention relates to a method of topical treatment of otitis externa, more particularly a method of treating otitis externa using one or more macrocyclic lactone compounds, more specifically, one or more avermectin compounds or milbemycin compounds.

BACKGROUND OF THE INVENTION

The external ear consists of the external auditory canal and the auricle. Otitis externa, sometimes called swimmer's ear or an external ear infection, is a commonly used term to define the infection or inflammation of the external auditory canal and auricle. Otitis externa may affect the entire ear canal, or just a small area within the canal. Otitis externa due to infection may be caused by a variety of bacteria or fungi. In addition, viral organisms are also causative of infective otitis externa. Otitis externa may also be caused by inflammation such as from a scratch, from chemical irritants in hair spray or hair dye, or even from water. Another common cause of otitis externa is the use of earplugs or wearing hearing aids. Otitis externa also occurs in many other species in addition to human.

Acute otitis externa is primarily of bacterial origin, and is often associated with high humidity, warmer temperatures and swimming. Glands within the canal secrete a waxy exudate known as cerumen which aids in trapping air born debris as well as acidifying the epithelial surface. Such acidification minimizes the overgrowth of bacteria. However, upon exposure to copious amounts of exogenous water such as, for example, swimming, the epithelial lining may become more alkaline, leading to an increased growth and over-growth in bacteria, and the resultant inflammatory response characteristic of otitis externa. Pathogens commonly associated with acute otitis externa are *Pseudomonas aeruginosa, Staphylococcus epidermides, Staphylococcus aureus,* and *Streptococcus pyogenes.* Fungi and yeast are usually found in patients with chronic otitis externa or those who are immunocompromised. Moreover, if there are chronic skin conditions that affect the ear canal skin, such as atopic dermatitis, seborrheic dermatitis, psoriasis or abnormalities of keratin production, or if there has been a break in the skin from trauma, even the normal bacteria found in the ear canal may cause infection and full-blown symptoms of otitis externa.

Acute otitis externa occurs rather suddenly, rapidly worsens, and becomes very painful and alarming. The ear canal has an abundant nerve supply, therefore, the pain is often severe enough to interfere with sleep. Temporary deafness may also result as swelling and discharge physically close off the ear canal and prevent conduction of ambient sound to the ear drum. In more severe or untreated cases, the infection can spread to the soft tissues of the face that surround the adjacent parotid gland and the jaw joint, making chewing painful. Most bouts of otitis externa clear within a week or so with ear drops or sprays. However, in some cases the otitis externa becomes chronic (persistent). This means it lasts longer than three months. Occasionally, it can last for several years.

Chronic otitis externa is commonly caused from a fungal or allergic origin. Although not caused by as many factors, chronic otitis externa is about ten times more prevalent than acute otitis externa. *Candida albicans* and *Aspergillus* species are the most common fungal pathogens responsible for the condition. Fungal ear canal infections, also known as otomycosis, range from inconsequential to very severe. Fungus can be saprophytic, in which there are no symptoms and the fungus simply co-exists in the ear canal in a harmless parasitic relationship with the host. If for any reason the fungus begins active reproduction, the ear canal can fill with dense fungal debris, causing pressure and ever-increasing pain that is unrelenting until the fungus is removed from the canal and anti-fungal medication is used. Most antibacterial ear drops also contain a steroid to hasten resolution of canal edema and pain. However, such drops make fungal infection worse. Prolonged use of them promotes growth of fungus in the ear canal.

In the past, otitis externa has been treated with topical application of antibacterial and antifungal agents, as well as anti-inflammatory agents. Broad spectrum topically effective antibiotic otic formulations containing antibacterial agents, such as neomycin sulfate, colistin sulfate, polymyxin b, or their combinations, have been utilized to destroy causative bacteria. Anti-mycotic topically acting agents, such as nystatin and clotrimazole, have been used to destroy underlying fungal disease. In addition, the anti-viral agent acyclovir has also been utilized to treat viral based otitis externa.

Anti-inflammatory agents, often included in the above mentioned otic formulations, have been used to control the inflammatory process of otitis externa. The anti-inflammatory agents include, for example, hydrocortisone, hydrocortisone acetate and dexamethasone sodium phosphate. The above described active agents are often used in combination to treat both the causative, for example, bacterial infection, as well as the inflammatory process itself. The otic formulations are often utilized in drop form for topical administration to the effected ear. In order to achieve a uniform delivery of a medication to the epithelial lining of the auditory ear canal, wicks, comprised of absorbent material such as cotton, are utilized to draw the suspensions into the ear canal.

Many otic drops also contain a topical anesthetic for immediate relief of pain caused by the infection or inflammation. However, there are disadvantages to include a topical anesthetic in the composition, because numbing the pain may mask symptoms of an advancing infection, and may hide symptoms that may cause serious if not permanent damage. Moreover, some topical anesthetics such as pramoxine is known to cause contact dermatitis or induce inflammation to an allergic response.

The macrocyclic lactones (avermectins and milbemycins) are products or chemical derivatives thereof, of soil microorganisms belonging to the genus *Streptomyces*. The avermectin series and milbemycin series of compounds are very potent antiparasitic agents, useful against a broad spectrum of endoparasites and ectoparasites in mammals and also having agricultural utilities against various nematode and insect parasites found in and on crops and in soil. Compounds of this group include avermectins, milbemycins, and their semi-synthetic derivatives, for example, ivermectin, doramectin, emamectin, eprinomectin, selamectin, latidectin, milbemectin, moxidectin, nemadectin, milbemycin oxime, and lepimectin. These chemicals have been described, for example, in U.S. Pat. Nos. 3,950,360, 4,199,569, 4,879,749 and 5,268,710. The avermectins and, to a lesser extent, the milbemycins, have revolutionized antiparasitic and antipest control over the past few decades.

In terms of their mechanism of action as antiparasitic agents, the avermectins block the transmittance of electrical activity in nerves and muscle cells by activating voltage dependent membrane-bound proteins containing chloride channels. Chloride channel blockers in both insects and mammals are highly toxic convulsants causing a hyperexcitation of the nervous system through antagonism of the inhibitory neurotransmitter GABA. Avermectin compounds effectively block GABA stimulated uptake and cause a release of chloride-channel dependent neurotransmitters. Milbemycin compounds have a similar mechanism of action, but a longer half-life than the avermectins. Milbemycin compounds open glutamate sensitive chloride channels in neurons and myocytes of invertebrates, leading to hyperpolarization of these cells and blocking of signal transfer.

Ivermectin has been used as an antiparasitic agent to treat various animal parasites and parasitic diseases since mid-1980's. It is commercially available for animal use as Cardomec™ (for felines), Zimecterin® (for equines) and Ivomec® (for bovines) by MERIAL Limited, Duluth, Ga. The medicine is available in tablets, paste, or chewables for heartworm prevention, topical solution for ear mite treatment, or as oral or injectable solution for other parasite problems.

Ivermectin is also commercially available from Merck & Co., Inc for human use under the tradename of Stromectol® for eradication of threadworm *Strongyloides stercoralis*, and for eradication of *Onchocerca volvulus*. The medicine is available in tablets and is orally administered by the patients. Magda et al. (*Amer. J. Trop. Med. Hyg.* 53(6) 1995 pp. 652-653) describe a method of topical application of ivermectin to treat head lice. U.S. Pat. No. 5,952,372 (to McDaniel) discloses a method of treating a form of rosacea associated with the ectoparasite Demodex by eliminating mites.

Recently, ivermectin has also been found useful in treating dermatological conditions. U.S. Pat. Nos. 6,133,310, 6,433, 006, 6,399,652, 6,399,651 and 6,319,945 (to Parks) disclose methods of treating acne rosacea, seborrheic dermatitis, acne vulgaris, transient acantholytic dermatitis, acne miliaris necrotica, acne varioliformis, perioral dermatitis, and acneiform eruptions by topically applying an avermectin compound, particularly ivermectin, to the affected areas.

It is also noted that the above described parasitic diseases and dermatological conditions by themselves are not the cause of otitis externa.

Because of the many causes described above, otitis externa is fairly prevalent, affecting about three to five percent of the population. Moreover, chronic otitis externa is much more prevalent than acute otitis externa. Therefore, there is a need for effective and improved otic compositions for treating otitis externa.

SUMMARY OF THE INVENTION

In one embodiment, the present invention is directed to a method of treating otitis externa comprising topically applying an otic composition comprising an effective amount of one or more macrocyclic lactone compounds including avermectin compounds, milbemycin compounds, or mixture thereof, and a pharmaceutically acceptable carrier to an affected ear of an individual suffering from otitis externa. The otic composition is applied into the external auditory canal and/or topically applied on the auricle of the affected ear.

In another embodiment, the present invention is directed to a composition comprising one or more avermectin compounds or milbemycin compounds, or mixtures thereof for treating otitis externa. Unless defined otherwise, all technical and scientific terms used herein have the same meaning as commonly understood by one having ordinary skills in the art to which the invention belongs.

The avermectin compounds in the otic composition include avermectins, or avermectin derivatives such as ivermectin, ivermectin derivatives, emamectin, doramectin, selamectin, eprinomectin, or latidectin. The milbemycin compounds include milbemycins, or milbemycin derivatives such as moxidectin, nemadectin, milbemycin oxime, or lepimectin. Preferably, the otic composition comprises an effective amount of ivermectin.

The advantages of the present invention will become apparent from the following description in conjunction with exemplary embodiments of the invention.

DETAILED DESCRIPTION OF THE INVENTION

In one embodiment, the present invention provides a method of treating otitis externa using one or more macrocyclic lactone compounds. The method comprises topically applying an otic composition comprising an effective amount of one or more macrocyclic lactone compounds including avermectin compounds, milbemycin compounds, or mixture thereof, and a pharmaceutically acceptable carrier to an affected ear of an individual suffering from otitis externa.

In another embodiment, the present invention provides the use of one or more macrocyclic lactone compounds including avermectin compounds, milbemycin compounds, or mixture thereof in the preparation of a pharmaceutical composition intended for the treatment of otitis externa. Unless defined otherwise, all technical and scientific terms used herein have the same meaning as commonly understood by one having ordinary skills in the art to which the invention belongs.

The macrocyclic lactone compounds for the purpose of the present invention include avermectin compounds and milbemycin compounds. The avermectin compounds for the purpose of the present invention include avermectins and derivatives thereof, which include, but not limited to, avermectin $A_{1a}$, $A_{1b}$, $A_{2a}$, $A_{2b}$, $B_{1a}$, $B_{1b}$, $B_{2a}$ and $B_{2b}$, ivermectin and derivatives thereof, emamectin, doramectin, selamectin, eprinomectin, latidectin, or mixtures thereof. The milbemycin compounds for the purpose of the present invention include milbemycins and derivatives thereof, which include, but not limited to, milbemycins, moxidectin, nemadectin, milbemycin oxime, milbemectin, lepimectin, or mixtures thereof.

In one embodiment, the otitis composition comprises one or more avermectin compounds and a pharmaceutically acceptable carrier or a medium which is suitable for application to the affected anorectal region, as described further in detail hereinafter. In another embodiment, the otitis composition comprises one or more milbemycin compounds and a pharmaceutically acceptable carrier or a medium which is suitable for topical application to the affected area of otitis externa, as described further in detail hereinafter. Preferably, ivermectin is used in the otitis composition.

The following molecular structure represents the avermectins, which can be chemically converted to useful derivatives as discussed below.

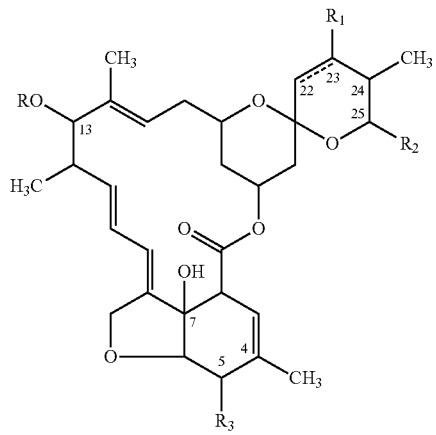

wherein the broken line at the 22-23 position represents an optional double bond; $R_1$ is hydroxy and is present only when the bond at the 22-23 position is a single bond; $R_2$ is isopropyl or sec-butyl; $R_3$ is methoxy or hydroxyl, and R is the 4'-(alpha-L-oleandrosyl)-alpha-L-oleandroside of the structure:

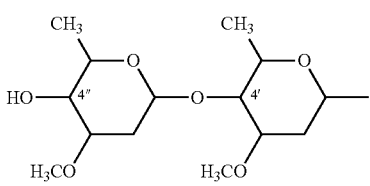 [SMILES: COC1CC(OC2C(C)OC(C)CC2OC)OC(C)C1O]

The naturally occurring avermectins are a series of 16-membered macrocyclic lactones isolated from fermentation products of *Streptomyces avermitilis*, a soil Actinomycete. There are eight different but closely related compounds produced by *Streptomyces avermitillis*, isolated in four pairs of homologue compounds with a major (a-component) and a minor (b-component) component, which are designated as avermectin $A_{1a}$, $A_{1b}$, $A_{2a}$, $A_{2b}$, $B_{1a}$, $B_{1b}$, $B_{2a}$, and $B_{2b}$. The mixture of avermectin $B_{1a}$ and $B_{1b}$, widely used insecticide and antihelmintic, are commonly referred to as abamectin. The production of these compounds is described in U.S. Pat. No. 4,310,519, which is incorporated herein by reference in its entirety. The structures of these eight individual compounds in reference to the above structural formula have been identified as follows:

|  | $R_1$ | $R_2$ | $R_3$ |
| --- | --- | --- | --- |
| $A_{1a}$ | Double bond | sec-butyl | —$OCH_3$ |
| $A_{1b}$ | Double bond | iso-propyl | —$OCH_3$ |
| $A_{2a}$ | —OH | sec-butyl | —$OCH_3$ |
| $A_{2b}$ | —OH | iso-propyl | —$OCH_3$ |
| $B_{1a}$ | Double bond | sec-butyl | —OH |
| $B_{1b}$ | Double bond | iso-propyl | —OH |
| $B_{2a}$ | —OH | sec-butyl | —OH |
| $B_{2b}$ | —OH | iso-propyl | —OH |

The 22, 23-double bond of some avermectins may be selectively reduced to prepare ivermectin and its derivatives. Ivermectin, a member of avermectin compound family, is a semi-synthetic derivative of avermectin and is generally produced as a mixture of 22,23-dihydroavermectin $B_{1a}$ and 22,23-dihydroavermectin $B_{1b}$. The preparation of ivermectin and derivatives are disclosed in U.S. Pat. No. 4,199,569, which is incorporated herein by reference in its entirety.

The following structural formula shows the structures of ivermectin and its derivatives:

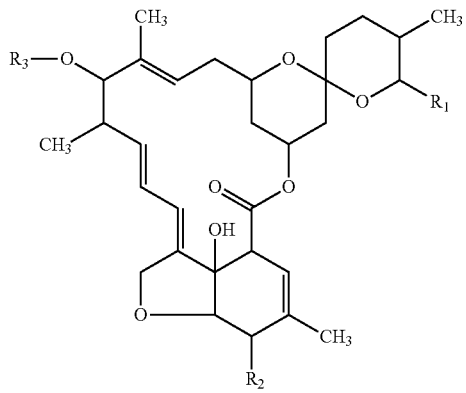

wherein $R_1$ is iso-propyl or sec-butyl; $R_2$ is methoxy, hydroxy or alkanoyloxy; $R_3$ is hydrogen; alkanoyl; alpha-L-oleandrosyl; 4'-alkanoyl-alpha-L-oleandrosyl; 4'-(alpha-L-oleandrosyl)-alpha-L-oleandrosyl; or 4"-alkanoyl-4'-(alpha-L-oleandrosyl)-alpha-L-oleandrosyl. Herein, the "alkanoyl" includes alkanoyl groups having 2 to 6 carbon atoms such as acetyl, propionyl, butyryl, and pivaloyl. Ivermectin and its derivatives shown above share profound anthelmintic, insecticidal, ectoparasiticidal and acaricidal activity.

Doramectin and eprinomectin are represented by the following structure:

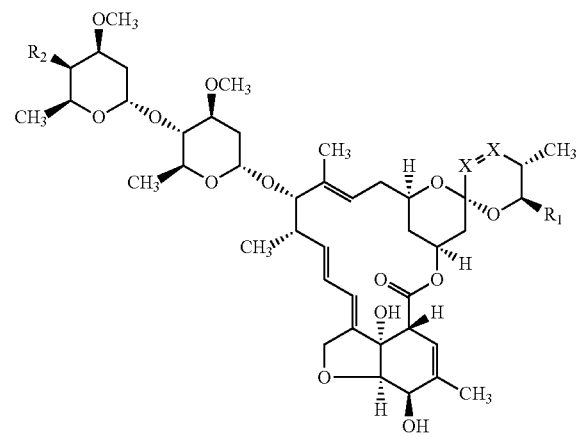

In doramectin, x=x is —CH=CH—, $R_1$ is —$C_6H_{10}$, $R_2$ is —OH. In eprinomectin, x=x is —CH=CH—; $R_1$ is —CH($CH_3$)$CH_2CH_3$, or —CH($CH_3$)$_2$; $R_2$ is —NHCOCH$_3$. These compounds are described in "Veterinary Parasitology", vol. 49, No. 1, July 1993, 5-15.

Selamectin has the following structure:

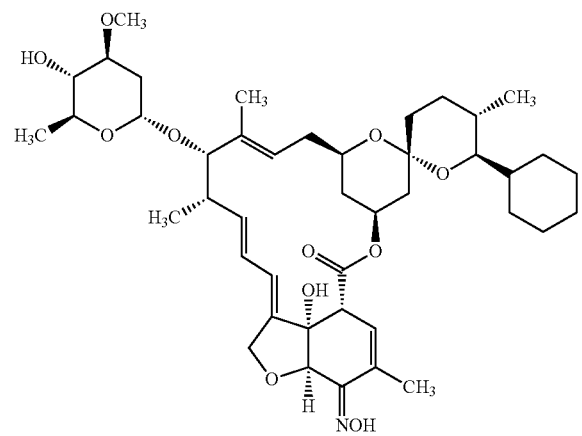

which is described in EP1142577A2 and WO 94/15944.

Emamectin has the following structure:

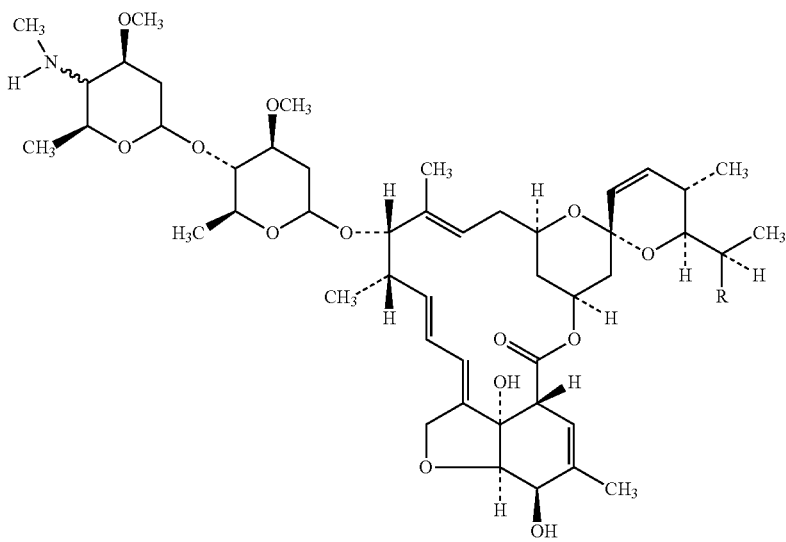

where R is —CH$_2$CH$_2$ or —CH$_3$. Emamectin and its salts are described in U.S. Pat. No. 4,874,749.

The structure of latidectin, which is a mixture of components A3 and A4, is shown below:

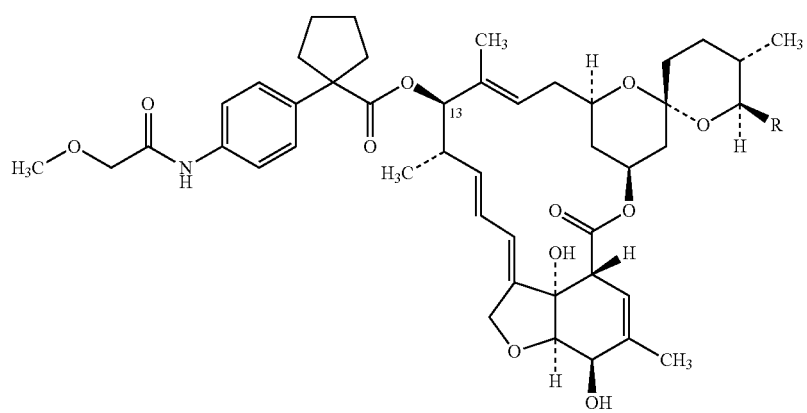

where component A3 has R=—CH$_2$CH$_3$, and component A4 has R=—CH$_3$.

Other avermectin derivatives are also known in the art. For example, the avermectins possess a disaccharide moiety at the C-13 position consisting of the alpha-L-oleandrosyl-alpha-L-oleandrosyl group. One or both of these saccharide groups may be removed as described in U.S. Pat. No. 4,206,205, and the produced aglycone derivatives have a hydroxy group at the 13-position. This group may be removed to form the 13-deoxy compound as described in U.S. Pat. Nos. 4,171,314 and 4,173,571, and the latter patent also describes the 13-halo derivatives. U.S. Pat. No. 5,077,308 describes avermectin aglycone derivatives which incorporate a ketal at C-13 position. The avermectins and derivatives have several hydroxy groups which may be acylated as described in U.S. Pat. No. 4,201,861. U.S. Pat. No. 5,055,454 describes avermectin derivatives in which position 13 of avermectin has been inverted from a normal alpha stereochemistry to the epimeric C-13 beta stereochemistry. U.S. Pat. No. 5,162,363 describes avermectin derivatives where the 23-position ring carbon atom is replaced with sulfur atom. U.S. Pat. No. 5,229,416 describes avermectin aglycone derivatives which incorporate two fluorine atoms at position 13 and 23. U.S. Pat. No. 5,262,400 describes avermectin compounds that have various substituents at the 4a-position including alkyl, alkoxy alkyl, or polyalkoxy alkyl groups. Other derivatives of avermectin and ivermectin are disclosed in U.S. Pat. Nos. 4,333,925, 4,963,667, 5,114,930, 5,350,742, and 5,830,875. All aforementioned patents are incorporated herein by reference in their entirety.

All ivermectin compounds mentioned above share the 16-membered macrocyclic lactone ring and the spectrum of anti-parasitic biological activity of ivermectin, varying only in degree. It is expected that they also share the activity spectrum of ivermectin suitable for the purpose of the present invention.

Like avermectins, milbemycins are products of fermentation by *Streptomyces* species, isolated from the fermentation broth of *Streptomyces hygroscopicus* subsp. *aureolacrimosus*. They have same mode of action, but a longer half-life than the avermectins. Milbemycins include a series and β series, which were initially named as B-41 antibiotics and given the designation A$_1$, A$_2$, A$_3$, A$_4$, B$_1$, B$_2$, B$_3$, C$_1$ and C$_2$, as described in U.S. Pat. Nos. 3,950,360 and 3,984,564. The B-41 designations are still commonly used today. The correlation of the initial designation to the nomenclature of α and β series of some milbemycins is described in U.S. Pat. No. 4,144,352. Within the family, milbemycins $\alpha_{11}$, $\alpha_{14}$, $A_3$ and $A_4$ have been found having the most effective acaricidal activity. A mixture of milbemycins $A_3$ and $A_4$ is commercialized under the name milbemectin.

The following structural formula represents milbemectin and several potent derivatives of milbemycins:

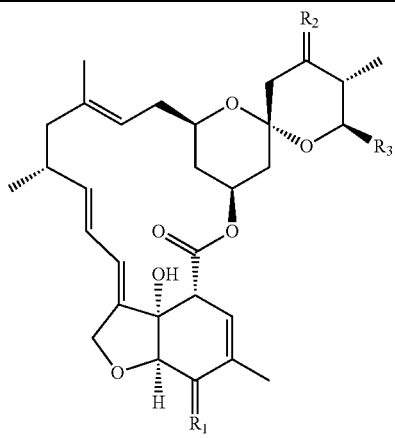

| | $R_1$ | $R_2$ | $R_3$ |
|---|---|---|---|
| Milbemectin | —H, (β)-OH | —H, —H | —CH$_3$; —CH$_2$CH$_3$ |
| Milbemycin oxime | =NOH | —H, —H | —CH$_3$; —CH$_2$CH$_3$ |
| Moxidectin | —H, (β)-OH | =NOCH$_3$ | (Z)—C(CH$_3$)=CH—CH(CH$_3$)$_2$ |
| Nemadectin | —H, (β)-OH | —H, (α)-OH | (Z)—C(CH$_3$)=CH—CH(CH$_3$)$_2$ |

Further description of milbemycins and their derivatives can be found in "Avermectins and Milbemycins", Davies H. G. et al., 1986, Nat. Prod. Rep., 3, 87-121; "Synthesis of Milbemycins from Avermectins", Mrozik H. et al., 1983, Tetrahedron Lett., 24, 5333-5336; and U.S. Pat. Nos. 4,134,973 and 4,144,352.

A further derivative of milbemycin is lepimectin, which has the following structure:

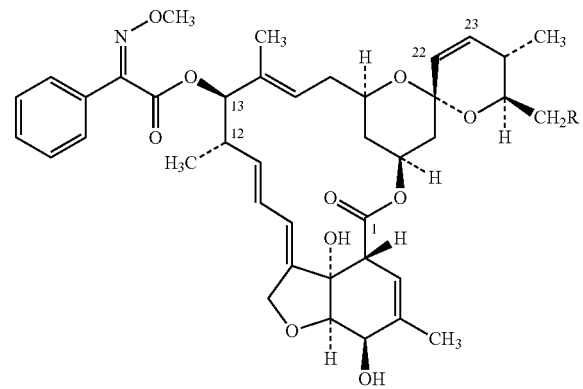

where R is —CH$_2$CH$_3$ (major component), and R is —CH$_3$ (minor component).

Both avermectins and milbemycins have macrocyclic lactone structures that are superimposable, they are produced by the same genus of soil dwelling organisms, they have the same mode of action, and they exert this action against the same nematode/acarine/insect spectrum of targets. It is expected that milbemycin compounds also share the activity spectrum of ivermectin suitable for the purpose of the present invention.

The concentration of the one or more avermectin compounds or the one or more milbemycin compounds in the composition for the purpose of the present invention can be greater than 0.001% weight by weight (w/w). In some embodiments, the concentration of the one or more avermectin compounds or the one or more milbemycin compounds in the otic composition is in a range from about 0.001% to about 10% (w/w), preferably from about 0.03% to about 5% (w/w), and more preferably from about 0.05% to about 3% (w/w). In a preferred embodiment, ivermectin is used. The concentration of ivermectin in the otic composition can be greater than 0.001% (w/w). In some embodiments, the concentration of ivermectin in the otic composition is from about 0.001% to about 10% (w/w), preferably from about 0.03% to about 5% (w/w), and more preferably from about 0.05% to about 3% (w/w). It has been found that the otic composition containing ivermectin at a concentration as low as 0.075% is effective, as illustrated in the examples hereinafter, in treating otitis externa. Such a low effective concentration is advantageous because it reduces risks of side effects and the possibility of triggering body's autoimmune responses.

The otic composition can be in various forms, including, but not limited to, solution, spray, gel, ointment, or emulsion in the form of liquid suspension, lotion, cream. The otic composition can also be integrated into an absorbent material, such as a wick of cotton fabric or medical dressing, which can be placed into the external auditory canal. Furthermore, the otic composition can also be in the form of suspensions of microspheres or nanospheres, lipid or polymeric vesicles, or polymeric patches or hydrogels for controlled release.

Pharmaceutically acceptable carriers or media suitable for topical application into the external auditory canal and the auricle are known to those skilled in the art. In some embodiments, the otic composition comprises one or more surfactants that enhance wetting of the external auditory canal and facilitate spreading of the otic composition on the epithelial lining of the external auditory canal. It is known that the cerumen exudate, normally secreted upon the epithelial tissue lining the external auditory canal, is a waxy material that imparts a high surface tension thereto which is useful in preventing foreign matter from reaching the tympanic membrane and effecting the middle and inner ear. During otitis externa, cerumen production increases in response to inflammation of the epithelial lining of the external auditory canal. Moreover, during otitis externa proteinaceous inflammatory waste materials resulting from the lysis, phagocytosis and necrosis of antigenic material secrete in the external auditory canal. These secreted substances form a coating upon the epithelial lining of the external auditory canal and tend to inhibit uniform or effective application of aqueous ear drops on the epithelial lining of the external auditory canal in the treatment of the inflammatory condition.

Surfactants are usually organic compounds that are amphiphilic, containing both hydrophobic tail groups and hydrophilic head groups. Surfactants reduce the surface tension of water by adsorbing at the liquid-gas interface, and reduce the interfacial tension between oil and water by adsorbing at the liquid-liquid interface. The surfactant in the otic composition functions as a wetting agent, which reduces surface tension of the external auditory canal. As such the otic composition containing suitable surfactants spreads more uniformly on the surface of the external auditory canal. Moreover, surfactant molecules form vesicles and/or micelles, which facilitate penetration and delivery of the dispersed macrocyclic lactone compound in the composition through the secreted substances into the tissue. Various commercial available surfactants can be used in the otic composition. The surfactants can be anionic, cationic, non-ionic, zwitterionic surfactants, or combinations thereof.

In one exemplary embodiment, the otic composition is in a form of lotion having substantially neutral pH from about 6 to about 7. Example 1 provides an exemplary otic composition comprising ivermectin in a lotion. As shown in the example, a commercially available moisturizing lotion manufactured by Galderma Laboratories, Inc. under the trade name Cetaphil® moisturizing lotion is used as the medium for ivermectin to form the otic composition. Cetaphil® moisturizing lotion contains purified water, glycerin, hydrogenated polyisobutene, cetearyl alcohol and ceteareth-20, macadamia nut oil, dimethicone, tocopheryl acetate, stearoxytrimethylsilane and stearyl alcohol, panthenol, farnesol, benzyl alcohol, phenoxyethanol, acrylates/C10-30 alkyl acrylate crosspolymer, sodium hydroxide, and citric acid.

In some embodiments, the otic composition is an emulsion with one or more macrocyclic lactone compound therein. More specifically, the otic composition comprises one or more avermectin compound or milbemycin compound, one or more solvents for the active agent, an oily phase, one or more surfactants as emulsifier, and water. The method of preparing an emulsion is known to those skilled in the art. The emulsion can be formulated into a solution, lotion, or cream. The emulsion can also be sprayable. Example 2 provides an exemplary otic composition, which is a cream containing 1% of ivermectin.

The otic composition in the form of ointments can be prepared using either an oleaginous base or medium or an absorbent base. The oleaginous base comprises fixed oils or hydrocarbons, such as white petrolatum or mineral oil. The absorbent base comprises an anhydrous substance or substances which can absorb water, for example anhydrous lanolin. Following formation of the base, the macrocyclic lactone compound is added to an amount affording the desired concentration to form the otic composition.

Furthermore, the otic composition of the present invention can be in the form of thermal responsive hydrogel suitable for delivering the active component across otic membrane. Upon applying to the external auditory canal, the composition can change from a liquid suspension to gel and forms a coating within the auditory canal. The adhesion to the surface can facilitate delivery of the active component across the epithelial lining.

The otic composition of the present invention described above is applied into the external auditory canal and on the auricle of the affected ear. The lotion, gel, or ointment can be applied with an applicator into the external auditory canal by the patient or others. Preferably, the applicator has a smooth surface, for example, a glass rod, coated with the lotion, gel, or ointment. Although cotton swab can be used, precaution should be exercised, because cotton swab is rough and it can cause irritation to the epidermis of the external auditory canal, and cotton residue left in the ear canal can cause further complication of the condition. The composition in the form of liquid suspension can be dropped or sprayed into the external auditory canal. The otic composition can be packaged for proper dosing by the patients. Moreover, the otic composition can also be integrated into or applied on an absorbent material, such as a strip of cotton fabric or medical dressing, and then the absorbent material is inserted into the external auditory canal by a physician as needed.

The otic composition can be applied to the affected ear one or more times a day, typically one to two times a day, when an acute otitis externa occurs. When the pain is severe, the otic composition can be applied more frequently to help alleviate the symptoms. It has been discovered by the inventors that topical application of the otic composition containing ivermectin is surprisingly effective in treating otitis externa, particularly at early onset of the condition. A dramatic resolution of the symptoms of acute otitis externa with a single topical application of the ivermectin lotion has been observed with many patients. Typically, the pain and swelling subside significantly in eight to twelve hours after the topical application. In early mild cases, improvements were observed in one or two hours.

Preferably, the otic composition is applied to the affected ear as described above at early onset of otitis externa. It has been found that when the otic composition is applied at the early onset of otitis externa, one time topical application is sufficient to effectively treat the condition in most cases. No further application or other treatments is needed after a single topical application of the instant otic composition. Such efficiency in the treatment of otitis externa is unexpected.

Examples 3 through 6 illustrate the effectiveness of the method of the present invention in treating otitis externa. As shown, after the patients suffering from acute otitis externa were treated with the instant otic composition containing 0.075% of ivermectin, a dramatic resolution of the symptoms was achieved within 24 hours.

Example 7 further illustrates an example of treatment of patients who historically had reoccurrences of otitis externa with the otic composition of the present invention. Over a period of about two years, these patients reported that one single application of the ivermectin lotion at the early onset of the condition resulted clearing of the symptoms overnight, and no severe conditions were developed since using the treatment of the present invention.

Although the applicants are not bound by any theoretical explanation as to why the composition and the method of the present invention are effective in treating otitis externa, presentation of certain theoretical understanding may be of value. Based on clinical observations by the inventors, it is believed that the efficacy of the topical otic composition and the method of the present invention in topical treatment of otitis externa is due in part to the anti-inflammatory property of ivermectin, along with its antiseptic properties. It is believed that ivermectin is an effective anti-inflammatory agent, which blocks certain mediators of inflammation, therefore, diminishes symptoms caused by inflammation. Moreover, in view of the effect of ivermectin on neural system, it may also have some direct effects on the neural receptors in the skin, which may contribute to the rapid pain relief observed clinically.

The otic composition containing ivermectin can be provided as a kit wherein the composition is packaged in a container. Instructions on how to use the otic composition in accordance with the present invention are included on or associated with the container, which provides detailed instructions for treating otitis externa. Optionally, the kit can further include one or more applicators.

The following examples are illustrative of the invention and are in no way to be interpreted as limiting the scope of the invention, as defined in the claims. It will be understood that various other ingredients and proportions may be employed, in accordance with the proceeding disclosure. It is further noted that the method of the present invention has been described in treating otitis externa in human, however, it can also be used for treating otitis externa of other mammals.

EXAMPLE 1

Composition A of an ivermectin lotion is prepared as follows: mix 0.04 g of Zimecterin® (manufactured by MERIAL Limited, Duluth, Ga.) which contains 1.87% ivermectin, sufficiently with 100 mg of Cetaphil® moisturizing lotion (manufactured by Galderma Laboratories, Inc.) to form an ivermectin lotion. The ivermectin concentration in the formed lotion is 0.075% (w/w).

Composition B of an ivermectin lotion is prepared as follows: mix 0.054 g of Zimecterin® containing 1.87% ivermectin sufficiently with 100 mg of Cetaphil® moisturizing lotion to form an ivermectin lotion. The ivermectin concentration in the formed lotion is 0.1% (w/w).

Other suitable compositions that can be made in accordance with Example 1 include ivermectin in the following concentrations: 0.01% 0.05%, 0.12%, 0.15%, 0.2%, 0.5%, 1%, and 2% (w/w) with Cetaphil® moisturizing lotion as a medium. Other compatible commercial available lotions can also be used as a medium or carrier.

EXAMPLE 2

The following emulsion is prepared with the method known in the art.

| Ingredients | Percentage (% w/w) |
| --- | --- |
| Ivermectin | 1.0 |
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH to 6.3 |
| Water | qs 100 |

The emulsion prepared is in the form of cream.

Operating with informed consent of individuals, individuals were treated with the otic composition and the method of the present invention for treating otitis externa, as described in Examples 3 to 7.

EXAMPLE 3

A 62-year old male presented with acute otitis externa, symptoms including pain, tenderness, and swelling of the right ear canal. This was precipitated by inadvertently failing to dry his right ear after swimming two days earlier. The patient was treated with Composition A of the ivermectin lotion of Example 1. The ivermectin lotion was gently applied to the vestibule and the ear canals using a finger to a depth that was tolerated. Then, a few minutes later, using a rounded applicator without cotton, the lotion was applied deeper into the external auditory canal to a depth of about 0.5 to about 1 cm. The patient was dispensed with a sample of the lotion to be applied as needed. The affected ear was free of pain and swelling in 24 hours.

EXAMPLE 4

A 22-year old female had been derelict in drying her ears after prolonged shampooing and rinsing episodes, which resulted in swelling and tenderness of both ears. Inspection showed boggy, tender, swollen tissues of the external ear canal, the tragus and the pinna. The patient was diagnosed with otitis externa, admonished to dry her ears better in the future. Composition A of the ivermectin lotion of Example 1 was applied into the external ear canal, and on the tragus and the pinna. A sample of the ivermectin lotion was provided to the patient for home use. The patient returned in five days and was very pleased that her ears had recovered in only two days.

EXAMPLE 5

A 7-year old male child presented with inflamed tissues in the left ear, resulting in edema, pain and tenderness. The precipitating cause was not known. The Composition B of ivermectin lotion of Example 1 was applied into the external auditory canal and on the vestibule of the affected ear, and a sample of the ivermectin lotion was provided for home use. The patient's mother reported two days later that total clearing of all symptoms had been accomplished.

EXAMPLE 6

A 14-year old male presented with acute otitis externa of the left ear. The tender, red, and swollen left ear occurred about two days after swimming. The patient was treated with Composition A of the ivermectin lotion of Example 1. The ivermectin lotion was applied to the vestibule and the ear canals. Within 24 hours, the pain, redness and swelling subsided dramatically. No further treatment was needed after one single course topical application.

A number of other patients of different age and gender with acute otitis externa after swimming were treated similarly using either Composition A or B of Example 1. A dramatic resolution of the conditions with a single course topical application of the ivermectin lotion was observed with these patients. Typically, the pain and swelling subside significantly in eight to twelve hours. In early mild cases, improvements were observed in one or two hours.

EXAMPLE 7

Several patients historically having reoccurrences of otitis externa were treated with Composition A or B of the ivermectin lotion of Example 1. The patients were instructed to topically apply the ivermectin lotion into the affected external ear cannel with a smooth applicator when early symptoms of the condition were observed. Over a period of about two years, these patients reported that when they felt irritation and a return of inflammation symptoms, after they forgot to dry the ears, one single application of the ivermectin lotion resulted clearing of the symptoms overnight, and no severe symptoms were developed.

In the above described informal trials, no adverse side effects or contra-indications were observed among the patients. The patients had no complaints of skin irritation, sensitivity or discomfort originating from the treatment.

Each patent, patent application, publication, text and literature article or report cited or indicated herein is hereby expressly incorporated by reference in its entirety.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

What is claimed is:

1. A method of treating otitis externa in human that is not caused by parasites, said method comprising topically applying an effective amount of one or more macrocyclic lactone compound to an affected ear of a person suffering from otitis externa that is not caused by parasites, wherein said macrocyclic lactone compound is avermectin compound, milbemycin compound, or mixtures thereof.

2. The method of claim 1, wherein said macrocyclic lactone compound is applied into the external auditory canal of the affected ear.

3. The method of claim 2, wherein said macrocyclic lactone compound is applied with an applicator, dropped, or sprayed into the external auditory canal.

4. The method of claim 1, wherein said macrocyclic lactone compound is topically applied on the auricle of the affected ear.

5. The method of claim 1, wherein said macrocyclic lactone compound is topically applied one or more times to the affected ear.

6. The method of claim 1, wherein said macrocyclic lactone compound is applied at early onset of the otitis externa.

7. The method of claim 1, wherein said avermectin compound is selected from the group consisting of avermectins, ivermectin, emamectin, doramectin, selamectin, eprinomectin, and latidectin.

8. The method of claim 1, wherein said milbemycin compound is selected from the group consisting of milbemycins, moxidectin, nemadectin, milbemycin oxime, milbemectin, and lepimectin.

9. The method of claim 1, wherein said macrocyclic lactone compound is from about 0.001% to about 10% (w/w) in a composition.

10. The method of claim 1, wherein said macrocyclic lactone compound is from about 0.03% to about 5% (w/w) in a composition.

11. The method of claim 1, wherein said macrocyclic lactone compound is from about 0.05% to about 3% (w/w) in a composition.

12. The method of claim 1, wherein said avermectin compound is ivermectin.

13. The method of claim 12, wherein said ivermectin is from about 0.001% to about 10% (w/w) in a composition.

14. The method of claim 12, wherein said ivermectin is from about 0.03% to about 5% (w/w) in a composition.

15. The method of claim 12, wherein said ivermectin is from about 0.05% to about 3% (w/w) in a composition.

16. The method of claim 1, wherein said macrocyclic lactone compound is in a lotion, cream, gel, solution, ointment, or spray.

17. The method of claim 1, wherein said macrocyclic lactone compound is integrated in an absorbent material, adapted to be placed into the external auditory canal.

18. The method of claim 1, wherein topically applying said macrocyclic lactone compound rapidly relieves pain and subsides swelling.

19. The method of claim 16, wherein topically applying said macrocyclic lactone compound subsides pain and swelling in eight to twelve hours.

20. The method of claim 1, wherein topically applying said macrocyclic lactone compound clears symptoms of the otitis externa in one or two days.

21. The method of claim 1, wherein topically applying said macrocyclic lactone compound diminishes symptoms caused by inflammation associated with the otitis externa.

* * * * *

UNITED STATES PATENT AND TRADEMARK OFFICE
CERTIFICATE OF CORRECTION

PATENT NO. : 8,901,090 B2  
APPLICATION NO. : 13/823330  
DATED : December 2, 2014  
INVENTOR(S) : L. Dean Parks et al.

Page 1 of 1

It is certified that error appears in the above-identified patent and that said Letters Patent is hereby corrected as shown below:

In the Claims

Column 16, line 30, change "claim 16" to --claim 1--

Signed and Sealed this
Thirty-first Day of March, 2015

Michelle K. Lee
*Director of the United States Patent and Trademark Office*